United States Patent [19]

Larkin

[11] 4,041,015

[45] Aug. 9, 1977

[54] MELT VISCOSITY STABILIZERS FOR VINYL CHLORIDE POLYMERS

[75] Inventor: William A. Larkin, Morristown, N.J.

[73] Assignee: M&T Chemicals Inc., Greenwich, Conn.

[21] Appl. No.: 591,109

[22] Filed: June 27, 1975

[51] Int. Cl.[2] .............................................. C08K 3/30
[52] U.S. Cl. ...................... 260/45.75 R; 260/45.7 S; 260/45.75 A; 260/45.75 W; 260/45.75 B; 260/45.75 C; 260/45.75 V
[58] Field of Search ...................... 260/45.75, 45.85 S, 260/45.78, 45.7 S, 45.7 ST

[56] References Cited

U.S. PATENT DOCUMENTS

| | | | |
|---|---|---|---|
| 2,115,053 | 4/1938 | Winkelmann | 260/45.7 ST |
| 2,476,862 | 8/1949 | Cox et al. | 260/45.7 ST |
| 2,557,474 | 6/1951 | Sanderson et al. | 260/45.7 ST |
| 2,563,772 | 8/1951 | Cheney | 260/45.75 P |
| 3,108,126 | 10/1963 | Crauland | 260/45.75 S |
| 3,890,276 | 6/1975 | Stapfer | 260/45.75 S |

OTHER PUBLICATIONS

ACS Div. Polymer Chemistry – Polymer Preprints, vol. 12, No. 1, Mar. 1971, pp. 795–803.
Journal of Polymer Science – Polymer Chemistry Edition – vol. 12, pp. 2305–2315, 1974.
*The Stabilization of Polyvinyl Chloride* – by Chevassus, (1963), pp. xi–30.

*Primary Examiner*—V. P. Hoke
*Attorney, Agent, or Firm*—Robert P. Auber; Kenneth G. Wheeless; Robert Spector

[57] ABSTRACT

The melt viscosity of vinyl chloride polymers is effectively stabilized using linear polysulfides containing specified elements or organic radicals as terminal groups on the chains of sulfur atoms.

3 Claims, No Drawings

MELT VISCOSITY STABILIZERS FOR VINYL CHLORIDE POLYMERS

BACKGROUND

This invention relates to stabilizing the viscosity of molten vinyl chloride polymers. This invention further relates to a means for extending the useful processing time of molten vinyl chloride polymers.

Polyvinyl chloride and most vinyl chloride copolymers are thermoplastic materials which melt and flow under the proper conditions of heat and pressure and can thereby be formed into useful articles. Conventional shaping techniques include calendering, injection and compression molding and extrusion. The temperature employed to shape vinyl chloride polymers using these techniques are conventionally 200° C and above. Maintenance of a substantially constant melt viscosity throughout the forming operation is critical if the articles produced are to exhibit uniform size, weight and other physical characteristics at high output rates. Variations in melt viscosity in the blow molding of bottles, for example, will result in bottles of varying wall thickness. In pipe extrusion, variations in wall thickness with weakening of the pipe results. If the viscosity decreases, extrusion rates will decrease resulting in increased costs; if the viscosity increases, more power will be required to operate the equipment. With some polymers, such as those based on vinyl chloride, the increased viscosity will lead to increased frictional heat and consequent degradation of the polymer. This degradation may be evident as changes in color, brittleness and in extreme cases, the polymer will cease to move out of the equipment, back pressure will increase and the equipment may be damaged. It is an object of this invention to provide polymer additives which control the melt viscosity of thermoplastic materials during processing. These additives may also improve other properties such as color. In addition, physical properties of the finished articles may be more uniform.

It has now been found that certain inorganic and organic polysulfides containing linear chains of three or more sulfur atoms are effective melt viscosity control agents for vinyl chloride polymers. Various elements or organic radicals are bonded to the two thermal sulfur atoms of the chain. These additional atoms or groups may impart other desirable properties to the vinyl chloride polymer.

SUMMARY OF THE INVENTION

The present invention provides a method for stabilizing the melt viscosity of vinyl chloride polymer compositions, the method consisting essentially of incorporating into said composition between 0.1 and 10%, based on the weight of said polymer, of a linear polysulfide of the general formula $A_x(S_z)_y$ wherein each A is individually selected from the group consisting of 1. elements exhibiting an atomic weight of between 6.9 and 209, inclusive and a valence $v$, the elements being in turn selected from groups I-A, I-B, II-A, II-B, III-A, IV-B, V-A, VI-B, VII-B and VIII of the periodic table, tin and lead,
2. monovalent radicals of the formula

ROOCR'—, $(RCOO)_{v-1}M$— and $R_2n$—, wherein $x$ is 1 when $v$ is even and $x$ is 2 when $v$ is odd, $y$ is 1 when $v$ is 1 or 2, $y$ is 2 when $v$ is 4 and $y$ is equal to $v$ when $v$ is 3 or 5, $z$ is an integer between 3 and 8, inclusive, M represents a polyvalent element selected from the groups I-B, II-A, II-B, III-A, IV-A, IV-B, V-A, VI-B, VII-B and VIII of the periodic table and having a valence of an absolute value $v'$, R is selected from the group consisting of alkyl radicals containing between 1 and 12 carbon atoms, inclusive, alkenyl and alkynyl radicals containing between 2 and 12 carbon atoms, inclusive, cycloalkyl, aryl, alkaryl and aralkyl radicals and R' represents an alkylene radical containing between 1 and 12 carbon atoms, inclusive.

DETAILED DESCRIPTION OF THE INVENTION

The prior art considers the present polysulfides to be salts of sulfanes, $(HS_zH)$, wherein $z$ represents an integer between 3 and 8. The two hydrogen atoms of the sulfane are replaced with the aforementioned radical A, which represents specified elements from the periodic table, as defined hereinbefore, or the residue of a carboxylic acid

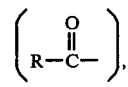

(ROOCR'—) or amine. In an alternative embodiment, A represents the residue of a half or partial salt of carboxylic acid and a polyvalent metallic Lewis base such as calcium or aluminum. For those metallic elements (M) with a valence of 3 or higher it will be understood that the remaining valences not specifically represented in the general formula

will be satisfied by bonds to a polysulfide chain or a carboxylic acid residue, depending upon the stoichiometry of the reactants (acid anhydride and polysulfide) employed to prepare the product.

The polysulfides of alkali and alkaline earth metals, particularly sodium and calcium, have been characterized and reported in the chemical literature. These compounds are conveniently prepared by heating an aqueous medium containing a suitable salt, oxide or hydroxide of the metal and a finely divided form of elemental sulfur. Calcium polysulfide reportedly can be represented by the formula $CaS_m$, wherein $m$ is 4 or 5. The number of sulfur atoms in the foregoing formula apparently represents an average value, since in aqueous solution an equilibrium is believed to exist that involves an intermolecular exchange of sulfur atoms and the formation of thiosulfate ions. While the foregoing formulae may not accurately represent the species that actually exist in the present polysulfides, this does not alter the fact that these compounds, when prepared as described in the accompanying specification and examples, are effective viscosity stabilizers for vinyl chloride polymer.

The present inorganic polysulfides are conveniently prepared by heating to between 40° C. and the boiling point an aqueous mixture containing finely divided sulfur and the oxide, hydroxide or other readily available salt of the desired element. Suitable salts include but are not limited to the halides, sulfate, sulfide and nitrate. Because many of the polysulfides are unstable in acidic media, salts which hydrolyze to yield an acidic solution should not be employed to prepare the polysulfide.

The reaction between the metal salt and sulfur is relatively slow and may require between 2 and 3 hours or longer to reach substantial completion. Some of the polysulfides, particularly those of the alkali metals and calcium, may not be stable in the dry state. These compounds and the other polysulfides can be added to vinyl chloride polymers as an aqueous solution.

The preparation of polysulfides from some heavy metal thiophenolates, notably those of lead, zinc, cadmium, mercury, copper, arsenic, antimony and bismuth, by reaction of these compounds with sulfur is disclosed in the chemical literature. These polysulfides can also be obtained using the methods described in the accompanying examples.

Organic polysulfides can be prepared by reacting sulfur or a sulfur chloride with salts of thiocarboxylic acids, for example potassium thiobenzoate or salts of mercaptoesters. Alternatively one can employ the anhydrides of monocarboxylic or dicarboxylic acids. Water soluble anhydrides such as acetic and propionic anhydrides should not be reacted in aqueous media, but rather one should employ anhydrous organic liquids such as hydrocarbons and ethers or mixtures thereof.

A preferred type of polysulfide contains both organic and inorganic radicals bonded to the two terminal sulfur atoms and is prepared by reacting an inorganic polysulfide, such as calcium sulfide, with a carboxylic acid anhydride. The number of moles of anhydride reacted is preferably equal to the number of moles of calcium or other metal present, such that half the total number of metal-sulfur bonds present in the original polysulfide are replaced by metal-oxygen bonds. When the metal (M) is divalent, the product is believed to have the structure

In accordance with this invention the foregoing classes of polysulfides are employed to stabilize the melt viscosity of vinyl chloride polymers. As used herein, the term "vinyl chloride polymers" encompasses homopolymers of vinyl chloride in addition to copolymers wherein at least 50% of the repeating units are derived from vinyl chloride. The remaining repeating units are derived from ethylenically unsaturated compounds which will copolymerize with vinyl chloride. Suitable comonomers include unsaturated hydrocarbons such as ethylene, propylene and styrene, unsaturated acids such as acrylic and maleic acid and esters derived from these acids, vinyl esters, including vinyl acetate, and other ethylenically unsaturated compounds such as acrylonitrile and 1-vinylpyridine.

Depending upon the degree of viscosity stabilization desired and the temperature at which the molten polymer will be processed, the concentration of polysulfide in the polymer formulation will be between 0.1 and about 10%, based on the weight of polymer.

The polysulfide is conveniently added to the vinyl chloride polymer together with other additives, including lubricants, pigments and antioxidants. The resultant formulation is then heated until a homogeneous melt is obtained, at which time it is shaped to the desired form by extrusion, molding, calendering or other suitable technique.

For greater convenience in handling and blending aqueous solutions of polysulfides, the solutions can be absorbed into particles of diatomaceous earth or other highly porous solid material that is subsequently incorporated into a polymer formulation.

The following examples demonstrate preferred embodiments of the present invention and should not be interpreted as limiting the scope thereof except as defined in the accompanying claims. All parts and percentages are by weight unless otherwise specified.

EXAMPLE 1

Preparation of Calcium Polysulfide

Calcium oxide (28 g.), 64 g. of U.S.P. grade sulfur and 500 cc. of water were heated with stirring. The color of the suspension turned from yellow to green when the temperature reached 85° C. As the temperature was increased to 98° C., the suspension became brown. When the temperature reached 130° C. the solid phase dissolved, yielding a dark brown-orange solution. The solution was then allowed to cool, with stirring, to ambient temperature. A 75 cc. portion of water was added to replace that lost by volatilization and the resultant liquid was filtered, yielding 500 g. of a wine colored solution. The solution was found to contain 9.69% sulfur and 3.14% calcium. The weight ratio of calcium to sulfur was 0.324. The calculated ratio for $CaS_4$ is 0.313, which is indicative of a high percentage of this entity in the solution.

EXAMPLE 2

Preparation of Barium Polysulfide

A 39.3 g. portion of barium oxide was added to distilled water which had been heated to a temperature of 96°-98° C. When the temperature of the water returned to 96°-98° C, 32 g. of sulfur were added. The mixture was maintained at this temperature for 1 hour with stirring, during which time the color of the solution changed from yellow to orange-brown. The reaction mixture was allowed to cool to ambient temperature and the solid phase isolated. The dried solid weighed 22.37 g.

EXAMPLE 3

Preparation of Magnesium Polysulfide

To 250 cc. of distilled water at a temperature of 95°-96° C. was added 10 g. of magnesium oxide. After fifteen minutes 32 g. of sulfur were added. Heating and stirring were continued for 1 hour, during which time a yellow precipitate formed. The precipitate was isolated when the reaction mixture had cooled to ambient temperature.

EXAMPLE 4

Preparation of Aluminum Polysulfide

A 32 g. portion of finely divided sulfur was added to an aqueous suspension containing 250 cc. of water and 19.5 g. of aluminum hydroxide. The suspension was heated to between 96° and 98° C. prior to the sulfur addition. The resultant mixture was heated for an additional hour, during which time a white precipitate formed. The precipitate was isolated, and subsequently evaluated as a viscosity stabilizer. The precipitate weighed 50.7 g.

EXAMPLE 5

Preparation of Lead Polysulfide

A 32 g. portion of sulfur was added to a stirred aqueous suspension containing 250 cc. of water and 55.8 g. of lead oxide (PbO). The suspension was maintained at a temperature between 94° and 95° C. prior to the sulfur addition and for 1 hour thereafter. The solid phase was then isolated, and subsequently evaluated as a viscosity stabilizer. The solid material weighed 87.35 g.

EXAMPLE 6

Preparation of Antimony Polysulfide

A 32 g. portion of sulfur was added to a stirred suspension containing 250 cc. of water and 132.9 g. of antimony trisulfate. The suspension was maintained at a temperature of 94°–5° C. prior to the sulfur addition and for 1.5 hours thereafter. The pH of the resultant solution was adjusted to between 9 and 10 using aqueous ammonium hydroxide. The water-insoluble solid phase was isolated and discarded. Upon evaporation of the water, an additional 76.2 g. of a solid was obtained. The water-soluble solid was subsequently evaluated as a viscosity stabilizer.

EXAMPLE 7

Preparation of Dibenzoyl Polysulfide

To a solution containing 18 g. (0.056 mole) of potassium thiobenzoate and 200 g. of chloroform at ambient temperature was added 7.7 g. (0.056 mole) of sulfur monochloride. The addition was dropwise and resulted in formation of a red precipitate. The precipitate which weighed 10.7 g. was isolated by filtration and used without further purification.

EXAMPLE 8

Preparation of Manganese Polysulfide

A solution containing 42.2 g. of manganese sulfate monohydrate and 250 cc. of water at a temperature of 94° C. was combined with 32 g. of sulfur. The resultant mixture was maintained at 94° C. and stirred for 1 hour, at which time sufficient solid sodium hydroxide was added to attain a pH of between 9 and 10. The mixture then turned a brownish yellow. Heating and stirring were continued for an additional hour, following which 36.1 g. of a solid material were isolated by filtration. An additional 47 g. of material was obtained following evaporation of the water.

EXAMPLE 9

Evaluation of Inorganic and Organic Polysulfides as Viscosity Control Agents The efficacy of the polysulfides described in the preceding examples as viscosity control agents for polyvinyl chloride was determined using a torque rheometer, which is capable of simulating the conditions of heat and pressure encountered in extruders, injection molders, calenders and other types of equipment commonly employed to process molten thermoplastic polymers. The torque rheometer consists of a mixing chamber containing a pair of helically shaped blades located along parallel axes. The blades rotate in opposite directions at a constant, predetermined speed. A polymer formulation, usually in the form of a finely divided powder, is introduced into the heated mixing chamber. The resultant melt is heated or cooled as required to maintain it at the desired temperature. The rotating blades are connected through a common link to a dynamometer which measures and records the torque required to maintain the predetermined speed. This speed was between 40 and 80 r.p.m. during the series of evaluations summarized in the following tables. The torque is measured in meter grams, and is directly proportional to the melt viscosity of the polymer formulation. Most desirably the torque should remain relatively constant throughout the period during which the polymer is in the molten state. The polysulfide compounds of Examples 2, 3, 4, 5, 6 and 7 were employed in solid form. Calcium polysulfide was added to the polymer formulation as an aqueous solution. All but two of the polymer formulations contained synthetic hydrous calcium silicate, which absorbed the polysulfide solution and made it esier to incorporate into the polymer formulation. Between 0.75 and 1.25 grams of calcium silicate was employed for each gram of polysulfide solution.

The following formulations were employed for the evaluations summarized in the accompanying table.

| A | |
|---|---|
| Medium Molecular Wt. Polyvinyl chloride | 100 parts |
| Paraffin wax | 1 part |
| B | |
| Medium Molecular Wt. Polyvinyl chloride (PVC) | 100 parts |
| Hydrocarbon wax (XL-165 S) | 1 part |
| Calcium stearate | 1 part |
| Surface treated calcium carbonate | 3 parts |
| Titanium dioxide (Omyalite 90T) | 2 parts |
| C | |
| High Molecular Wt. PVC | 100 parts |
| Calcium silicate | 2.3 parts |
| D | |
| Medium Molecular Wt. PVC | 100 parts |
| Calcium silicate | 2.3 parts |
| E | |
| Low Molecular Wt. PVC | 100 parts |
| Calcium silicate | 2.3 parts |
| F | |
| Vinyl chloride homopolymer modified with polypropylene | 100 parts |
| Calcium silicate | 2.3 parts |
| G | |
| Vinyl chloride/vinyl acetate copolymer (90/10) | 100 parts |
| Calcium stearate | 1 part |
| Calcium silicate | 2.3 parts |

All but one of the polysulfides described in the preceding Examples 1–8 was evaluated in one or more of the aforementioned formulations A through G. The time required to completely fuse the mixture in the mixing chamber of the torque rheometer together with the initial torque and the length of time between fusion and the onset of degradation, as evidenced by an abrupt increase in the torque value are set forth in the following table.

Unless otherwise indicated, the polysulfides were employed in the final form disclosed in the corresponding example. The calcium polysulfide employed in formulation B was combined with about 2.2 parts of calcium silicate prior to being combined with the other components of the formulation.

| Stabilizer of Example (parts) | Formulation | Fusion Time (min.) | Torque of Melt[1] (meter grams) | Period of Stable Viscosity (min.) |
|---|---|---|---|---|
| None (control) | A | 1.4 | 2800 | 6.5 |
| 2 (2) | A | 2.0 | 2650 | 19.6 |
| 3 (1) | A | 1.7 | 2650 | 17.0 |
| 4 (2) | A | 3.0 | 2650 | 14.3 |
| 5 (2) | A | 1.2 | 2650 | 20.0 |
| 6 (2) | A | 1.2 | 2750 | 10.0 |
| 9 (2) | A | 1.5 | 2600 | 14.1 |
| None (control) | B | 4.7 | 1800 | 3.7 |
| 1 (0.5) | B[3] | 2.0 | 2230 | 19.3 |
| sodium polysulfide (0.4) | B[4] | 3.0 | 1800 | 17.0 |
| 7 (2.0) | B | 5.0 | 2400 | 19.6 |
| TTBI[2] (2.0) | B | 3.5 | 2050 | 18.0 |
| None | C | 1.3 | 2900 | 4.8 |
| 1 (0.5) | C | 2.2 | 2900 | 7.0 |
| None | D | 1.4 | 2800 | 6.5 |
| 1 (0.5) | D | 0.7 | 2500 | 8.0 |
| sodium polysulfide (0.7) | D | 0.4 | 2350 | 8.0 |
| None | E | 0.2 | 1650 | 10.8 |
| 1 (0.5) | E | 0.3 | 1700 | 23.2 |
| None | F | 0.5 | 2100 | 11.6 |
| 1 (0.5) | F | 0.5 | 1800 | 50.0 |
| None | G | 0.5 | 2300 | 6.0 |
| 1 (0.5) | G | 0.4 | 2300 | 19.2 |

Notes:
[1]Represents average value observed following fusion and prior to onset of degradation
[2]Tetrathio bis(isooctyl acetate)
[3]Contains 2 parts calcium silicate
[4]Contains 0.8 part calcium silicate

What is claimed is:

1. A method for stabilizing the melt viscosity of vinyl chloride polymer compositions said method consisting essentially of incorporating into said composition between 0.1 and 10%, based on the weight of the vinyl chloride polymer, of a linear polysulfide of the general formula $A_x(S_z)_y$ wherein each A is individually selected from the group consisting of elements exhibiting an atomic weight of between 6.9 and 209, inclusive and a valence $v$, the elements being in turn selected from groups I-A, I-B, II-A, II-B, III-A, IV-B, V-A, VI-B, VII-B and VIII of the periodic table, tin and lead, wherein $x$ is 1 when $v$ is even and $x$ is 2 when $v$ is odd, $y$ is 1 when $v$ is 1 or 2, $y$ is 2 when $v$ is 4 and $y$ is equal to $v$ when $v$ is 3 or 5, and $z$ is an integer between 3 and 8, inclusive.

2. The method of claim 1 wherein each A represents the element calcium, sodium, barium, magnesium, aluminum, lead, antimony or manganese.

3. The method of claim 1 wherein the vinyl chloride polymer is a homopolymer or a copolymer of vinyl chloride with propylene, ethylene or vinyl acetate.

* * * * *